(12) United States Patent
Brüssermann et al.

(10) Patent No.: US 7,770,434 B2
(45) Date of Patent: Aug. 10, 2010

(54) SYSTEM AND METHOD FOR IN-PROCESS INTEGRITY TEST OF A FILTER

(75) Inventors: Michael Brüssermann, Münster (DE); Josef Dühnen, Bochum (DE); Stefan Riese, Münster (DE)

(73) Assignee: General Electric Company, Schenectady, NY (US)

( * ) Notice: Subject to any disclaimer, the term of this patent is extended or adjusted under 35 U.S.C. 154(b) by 637 days.

(21) Appl. No.: 11/411,771

(22) Filed: Apr. 27, 2006

(65) Prior Publication Data

US 2007/0251299 A1 Nov. 1, 2007

(51) Int. Cl.
*G01N 15/08* (2006.01)
(52) U.S. Cl. ............................................ 73/38
(58) Field of Classification Search .................. 73/38; 210/90
See application file for complete search history.

(56) References Cited

U.S. PATENT DOCUMENTS

| 2,819,608 | A | * | 1/1958 | McLaren et al. ............... 73/38 |
| 3,422,667 | A | * | 1/1969 | Hrdina ..................... 73/53.01 |
| 4,344,429 | A | * | 8/1982 | Gupton et al. ............... 604/67 |
| 4,744,240 | A | | 5/1988 | Reichelt ...................... 73/38 |
| 4,779,448 | A | | 10/1988 | Gogins .......................... 73/38 |
| 4,872,974 | A | * | 10/1989 | Hirayama et al. ............. 210/90 |
| 5,064,529 | A | * | 11/1991 | Hirayama et al. ............. 210/90 |
| 5,072,595 | A | * | 12/1991 | Barbier ......................... 62/129 |
| 5,960,129 | A | * | 9/1999 | Kleinschmitt ................ 385/12 |
| 6,568,282 | B1 | | 5/2003 | Ganzi ....................... 73/861.42 |
| 2003/0159977 | A1 | | 8/2003 | Tanny et al. ................... 210/90 |

FOREIGN PATENT DOCUMENTS

| DE | 33 12 729 | 10/1984 |
| EP | 0 396 258 | 11/1990 |
| EP | 0 958 852 | 12/1997 |

OTHER PUBLICATIONS

Maik W. Jornitz, Pharmaceutical Technology: The integrity tests: choosing diffusive airflows or bubble point:, p. 1-8, Jan. 31, 2002.
www.scottlaboratories.com/products, Mar. 24, 2006, "Bubble Point Test".

* cited by examiner

*Primary Examiner*—Hezron Williams
*Assistant Examiner*—Tamiko D Bellamy
(74) *Attorney, Agent, or Firm*—Hunton & Williams, LLP

(57) ABSTRACT

The invention relates to a method for in-process integrity test of a filter. The method may comprise the steps of: coupling a gas source to an input side of a filter without removing the filter from a dispenser system, the gas source supplying a gas and controlling a pressure of the gas; coupling a tube to an output side of the filter, the tube being filled with a liquid; increasing the pressure while monitoring the tube, with a light beam, for a displacement of the liquid by one or more gas bubbles; and determining a value of the pressure at which the displacement of the liquid is detected.

13 Claims, 5 Drawing Sheets

SYSTEM AND METHOD FOR IN-PROCESS INTEGRITY TEST OF A FILTER

BACKGROUND OF THE INVENTION

The present invention relates generally to the field of radiopharmacy and more particularly to a system and method for in-process integrity test of a filter in a dispenser system.

Radioactive parenterals (or injectable medicine) are widely used for medical imaging, such as, for example, positron emission tomography (PET). PET scanning technique is commonly used in clinical medicine and biomedical research to create images of a living body in its active state. PET scanners can produce images that illustrate various biological processes and functions. In a PET scan, the patient is initially injected with a radioactive substance known as a "radioactive tracer" or "radiotracer" that can become involved in certain physiological processes in the patient's body. Typical positron-emitting radiotracers contain isotopes such as, for example, $^{11}C$, $^{13}N$, $^{15}O$ and $^{18}F$. When positrons are emitted within the patient's body, they recombine with electrons in the neighboring tissues and become annihilated. The annihilation event typically results in a pair of gamma photons being released in opposite directions. One or more detector rings then detect these gamma photons, and the detection data are processed to reconstruct two-dimensional (2-D) or three-dimensional (3-D) tomographyic images.

Preparation of radiotracers is an important step for medical imaging (e.g., PET scans). Due to their radioactivity, radiotracers are preferably handled in automated dispenser systems. In such dispenser systems, before a vial is filled with a radiotracer having a specified radioactivity and volume, the radiotracer is typically flowed through a sterile filter to reduce bacteria and particulate content. A portion of a conventional radiotracer dispenser system is shown in FIG. 1. In this radiotracer dispenser system, a liquid radiotracer 10 is flowed from a bulk container (not shown), via a tube 103, a sterile filter 106 and another tube 104 before it eventually fills a vial 102. The tube 103 is coupled to the sterile filter 106's input side (12), and the tube 104 is coupled to the sterile filter 106's output side (14). The sterile filter 106 helps remove bacteria and/or particulate from the radiotracer 10.

During operation of a radiotracer dispenser system, the sterile filter therein has to undergo one or more integrity tests, for example, before and after a filling process. The integrity tests are performed to ensure the sterile filter meets specification and the filter membrane is intact during filtration. Conventionally, the integrity tests of sterile filters are carried out in special devices separate from a radiotracer dispenser system. That is, a sterile filter has to be manually removed from the dispenser system for an integrity test. This conventional approach poses a number of problems.

For example, instead of testing a sterile filter immediately after a radiotracer dispensing operation, it is desirable to wait until radioactivity of the radiotracer residue in the filter has decayed to a safe level. However, since a short-lived radiotracer has to be injected into a patient soon after it is dispensed, a delayed integrity test would be too late to prevent injection of a defective sample/batch. The only alternative, then, is for the personnel to remove the filter and start testing it immediately after a dispensing operation, thereby risking exposure to strong radiations.

In addition, it takes time for a sterile filter to be removed and tested elsewhere, and for a new filter to be installed. Therefore, with the conventional approach, it is impracticable to perform frequent integrity tests, and it is difficult to predict the remaining lifetime of a sterile filter. The useful life of a sterile filter is often conservatively estimated, after which time period the filter is tested for integrity. If the filter fails the integrity test, the radiotracer batch that has just been dispensed through this filter must be disqualified. Even if the filter passes the integrity test and still has some remaining useful life, it will be discarded.

BRIEF SUMMARY OF THE INVENTION

The present invention is directed to a system and method for in-process integrity test of a filter that overcomes these and other drawbacks of known systems and methods.

According to one embodiment, the invention relates to a method for in-process integrity test of a filter. The method may comprise the steps of: coupling a gas source to an input side of a filter without removing the filter from a dispenser system, the gas source supplying a gas and controlling a pressure of the gas; coupling a tube to an output side of the filter, the tube being filled with a liquid; increasing the pressure while monitoring the tube, with a light beam, for a displacement of the liquid by one or more gas bubbles; and determining a value of the pressure at which the displacement of the liquid is detected.

According to another embodiment, the invention relates to a system for in-process integrity test of a filter. The system may comprise: a gas source coupled to an input side of a filter while the filter is still installed in a dispenser system, the gas source capable of supplying a gas and controlling a pressure of the gas; a tube coupled to an output side of the filter, at least one portion of the tube being not opaque, wherein the at least one portion of the tube can be filled with a liquid; a light source, on one side of the at least one portion of the tube, that is capable of passing a light beam at least once through the at least one portion of the tube; and a detector configured to detect the light beam after the light beam has passed at least once through the at least one portion of the tube, wherein the detection of the light beam indicates whether the liquid is displaced from the at least one portion of the tube by one or more gas bubbles.

It is a technical advantage of the present invention that a system and method for in-process integrity test of a filter is disclosed. It is another technical advantage of the present invention that a sterile filter may be tested in process immediately after it dispenses a radiotracer. It is a further technical advantage of the present invention that a sterile filter in a radiotracer dispenser system may be tested without removing the filter from the dispenser system. It is an additional technical advantage of the present invention that an in-process integrity test of a filter minimizes human exposure to radiations.

BRIEF DESCRIPTION OF THE DRAWINGS

In order to facilitate a fuller understanding of the present invention, reference is now made to the appended drawings. These drawings should not be construed as limiting the present invention, but are intended to be exemplary only.

DETAILED DESCRIPTION OF THE INVENTION

Embodiments of the present invention provide a technique for in-process integrity test of a filter. The technique may be implemented in a new or existing radiotracer dispenser system to test the integrity of a sterile filter without removing it from the dispenser system. The integrity test may be performed frequently, safely and efficiently, and a test result may be obtained immediately after a dispensing operation. In addition, a calibration procedure may ensure the test results are accurate and reliable.

Figure 1:
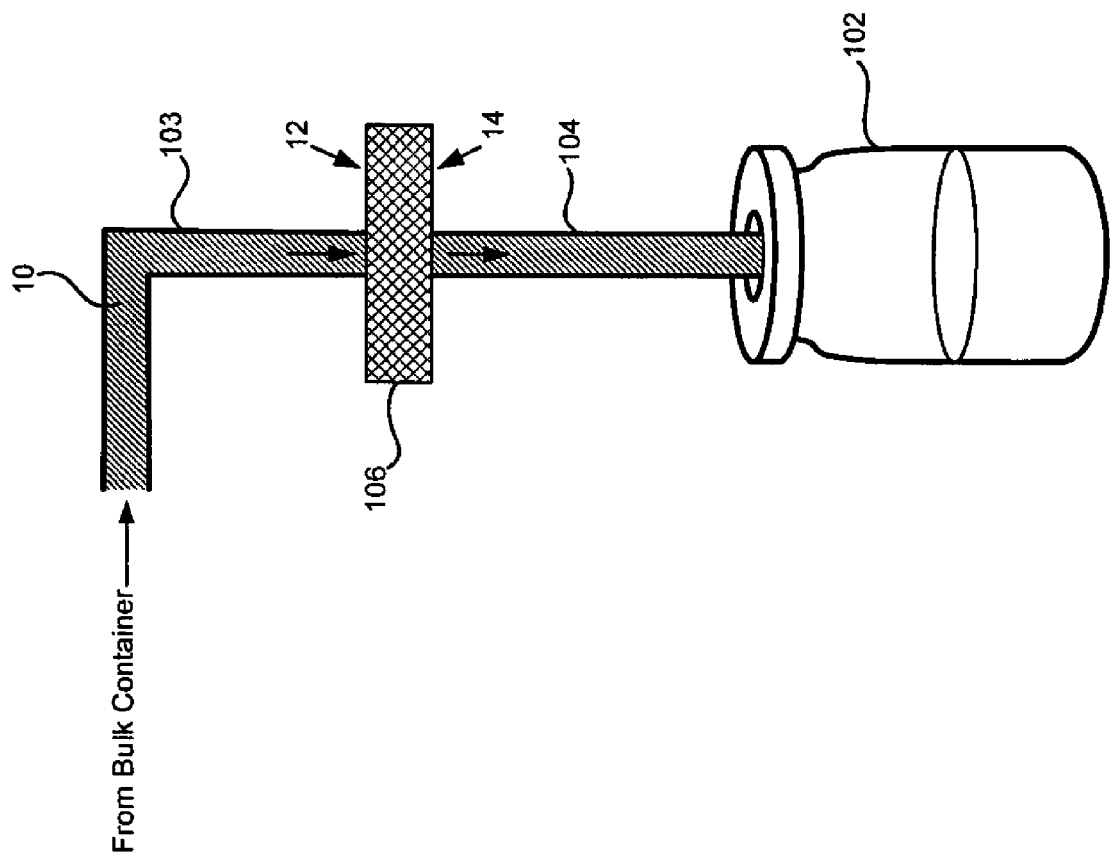
FIG. 1 shows a portion of a conventional radiotracer dispenser system.
Figure 2:
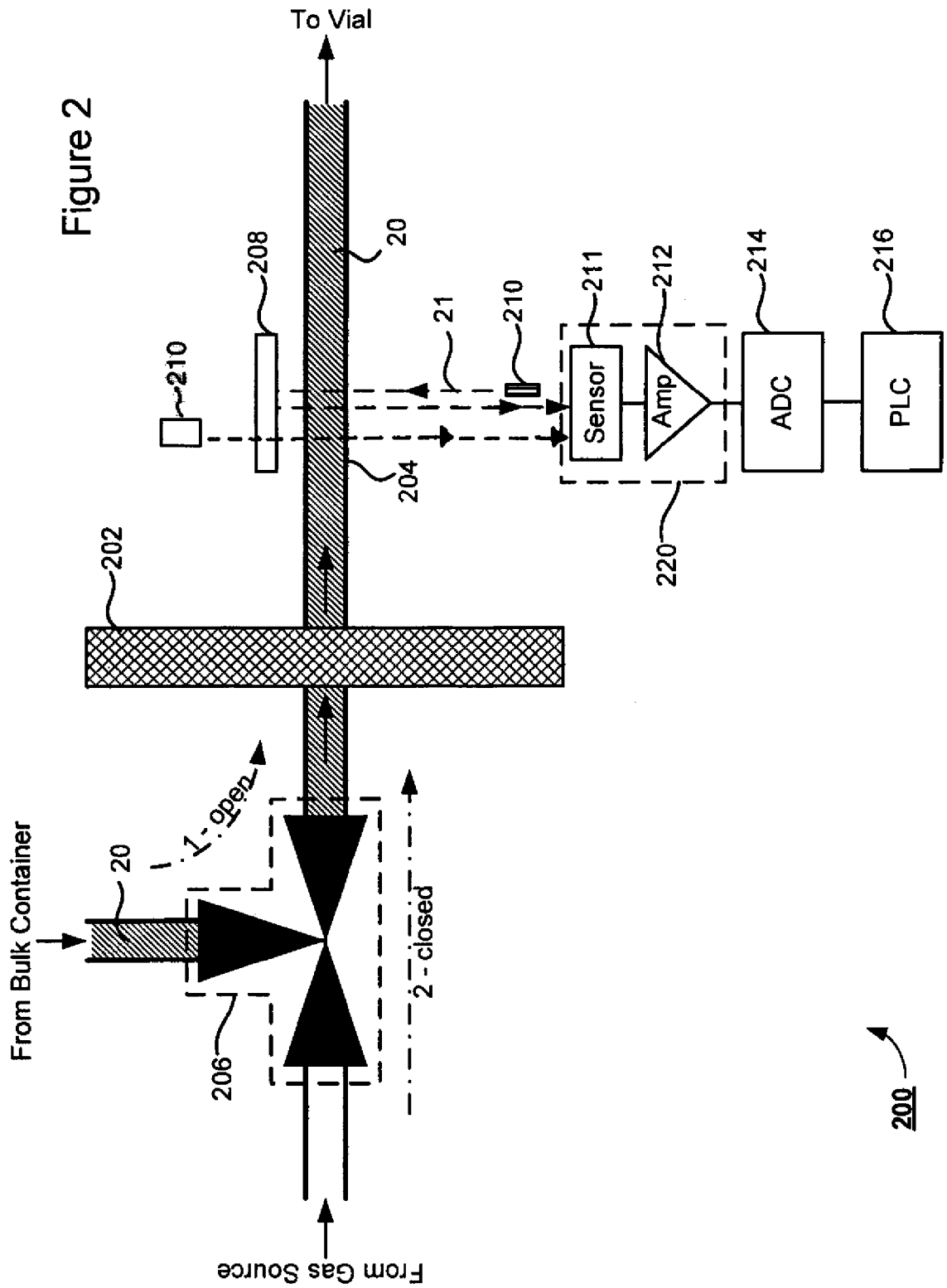
FIG. 2 is a diagram illustrating an exemplary system for in-process integrity test of a filter according to an embodiment of the present invention.

Referring to FIG. 2, there is shown a diagram illustrating an exemplary system 200 for in-process integrity test of a filter according to an embodiment of the present invention. The system 200 may be used to test the integrity of a sterile filter 202 within a radiotracer dispensing system (not shown). During a dispensing operation, the sterile filter 202 may receive, from a bulk container (not shown), a liquid 20 (e.g., a radiotracer), filter it, and output it to a vial (not shown). Without removing the sterile filter 202 from the dispenser system, a pressure-controlled gas source (not shown) may be coupled to the input side of the sterile filter 202. According to one embodiment, a medical three-way switch 206 may be preferably used to allow the input side of the sterile filter 202 to be either coupled to the bulk container or the gas source. As shown in FIG. 2, the three-way switch 206 may be in a dispensing mode, wherein a first channel between the bulk container and the sterile filter 202 is open and a second channel between the gas source and the sterile filter 202 is closed.

The output side of the sterile filter 202 may be coupled to a tube 204. At least a portion of the tube 204 is preferably not opaque, but at least partially transparent, to a light beam 21 generated from a light source 210. The light source 210 may be positioned on one side of the tube 204 and may direct the light beam 21 to pass through the tube 204. Alternatively, one or more optical fibers (not shown) may be used to direct the light beam 21 towards the tube 204. The light beam 21 may pass through the tube 204 at least once, preferably traversing an axis of the tube 204.

A detector 220 may be provided to detect the light beam 21 after it has passed through the tube 204 at least once. The detector 220 may comprise a photoelectric sensor 211 and an amplifier 212, and may be further coupled to an analog-to-digital converter (ADC) 214 and a programmable logic control (PLC) unit 216. The photoelectric sensor 211 may detect an optical signal (e.g., the light beam 21) and convert it into an electrical signal. The amplifier 212 may amplify the electrical signal before it is converted to a digital signal by the ADC 214 and then processed by the PLC unit 216. The PLC unit 216 may have additional functions such as, for example, controlling a gas pressure of the gas source, recording and analyzing the digital detection signal, and/or reporting integrity test results.

In the embodiment shown in FIG. 2, the detector 220 is positioned on the same side as the light source 210. In addition, a reflector 208, such as a mirror or a reflection plate, may be positioned on the other side of the tube 204, such that the light beam 21 may be reflected, pass through the tube 204 a second time, and be detected by the detector 220. Alternatively, in another embodiment, the detector 220 may be located on the other side of the tube 204 so as to detect the light beam 21 after it has passed once through the tube 204. The light source 210 may be integrated with at least a portion of the detector 220. For example, in one embodiment, the light source 210, the photoelectric sensor 211 and the amplifier 212 may be combined in a single unit that emits the light beam 21, detects the reflected light, and amplifies it.

Using the light beam 21 as a probe, the detector 220 may monitor the tube 204 for any displacement of the liquid 20 therein. Specifically, the detector 220 may be configured to distinguish between at least two levels of signal strength that correspond, respectively, to a liquid-filled (or full) tube and a gas-filled (or empty) tube.

Figure 3:
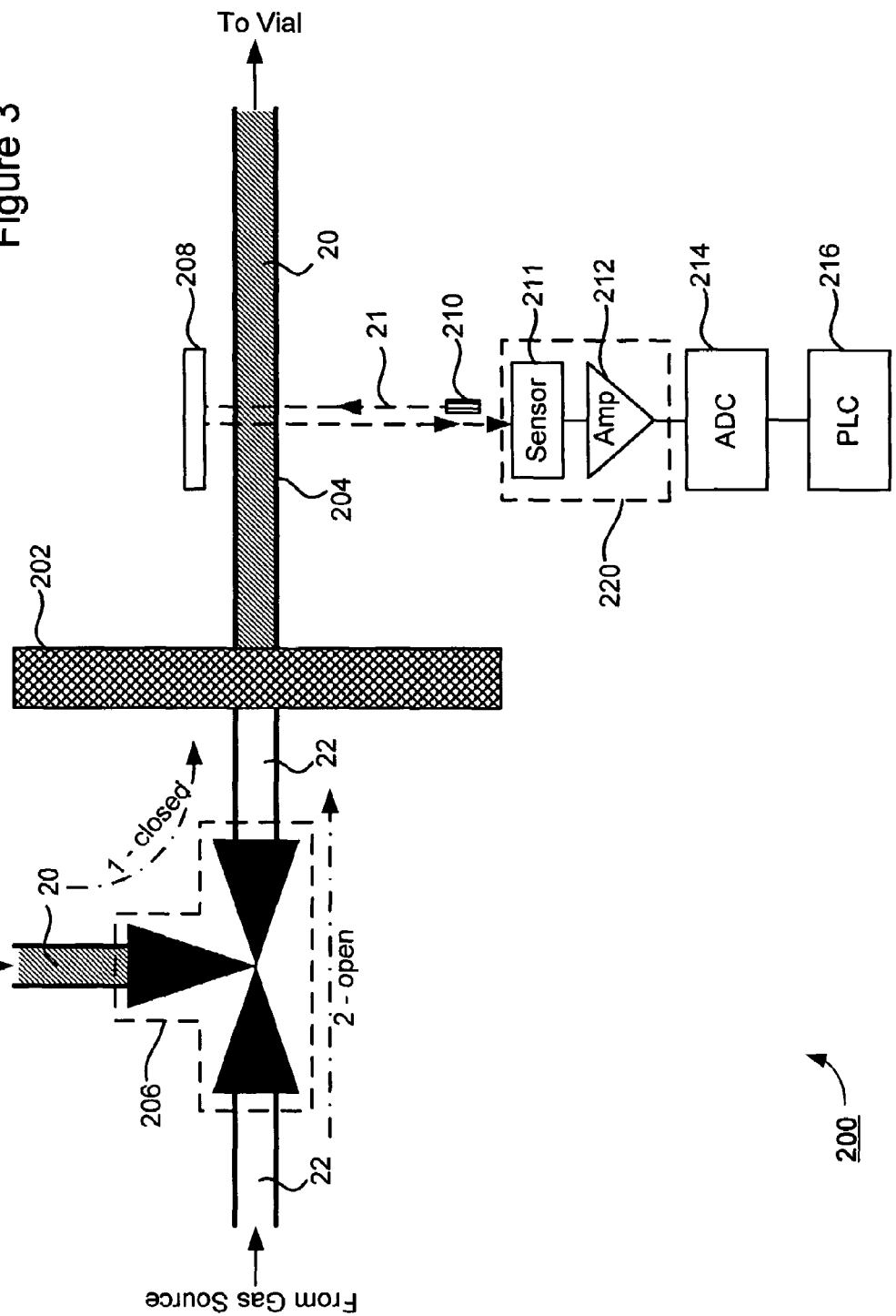
FIGS. 3 and 4 are diagrams illustrating the system of FIG. 2 in an exemplary in-process integrity test according to an embodiment of the present invention.
Figure 4:
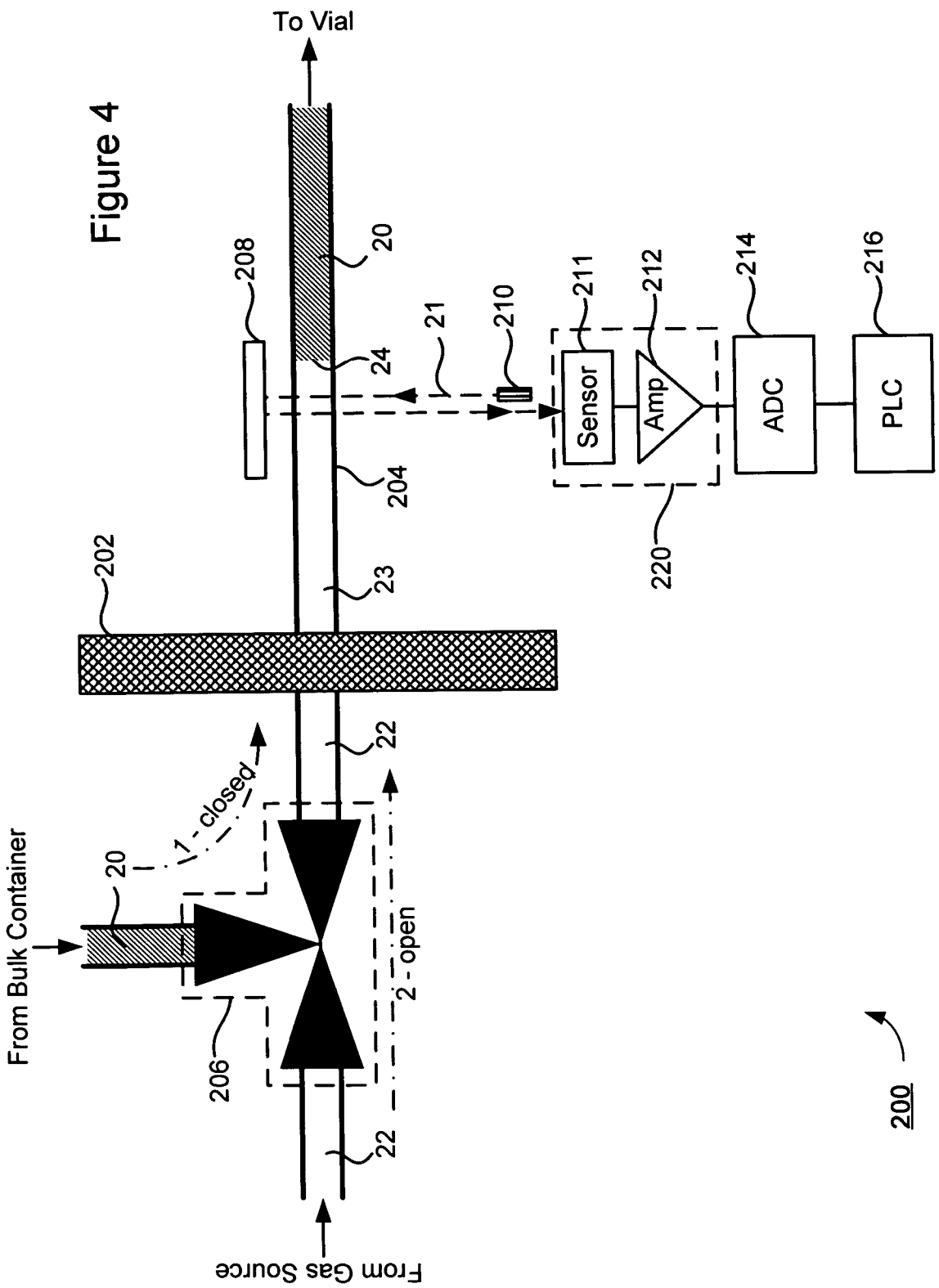

FIGS. 3 and 4 are diagrams illustrating the system 200 in an exemplary in-process integrity test of the sterile filter 202 according to an embodiment of the present invention.

FIG. 3 illustrates a first part of the integrity test wherein the three-way switch 206 is toggled to a testing mode. That is, the supply of the liquid 20 to the sterile filter 202 is stopped by closing that first channel between the bulk container and the sterile filter 202, while the second channel is open for the gas source to supply a gas 22 to the input side of the sterile filter 202. A pressure of the gas 22 may be gradually increased. As the pressure increases, the liquid 20 on the input side of the sterile filter 202 may be displaced and pushed to the output side. However, unless the pressure is high enough, the wetted membrane of the sterile filter 202 will block the gas 22 from penetrating to the output side of the sterile filter 202. Therefore, as shown in FIG. 3, a tube on the input side of the sterile filter 202 is filled with the gas 22, and the tube 204 on the output side is filled with the liquid 20. The gas pressure on the left is balanced mainly against a membrane pressure in the sterile filter 202. In coordination with the increase of the gas pressure, the detector 220 may be monitoring the liquid 20 in the tube 204 for any displacement of the liquid 20.

FIG. 4 illustrates a second part of the integrity test where a displacement of the liquid 20 is detected. As the gas pressure increases, the gas 22 may eventually start to penetrate the sterile filter 202, thereby displacing the liquid 20 and forming a bubble 23 on the output side of the sterile filter 202. The bubble 23 and the liquid 20 may share a boundary 24. As soon as the gas-liquid boundary 24 is pushed past the light beam 21, the detector 220 will start detecting a gas-filled (or empty) tube instead of a liquid-filled (or full) tube. The value of the gas pressure upon detection of the transition from a full tube to an empty tube may be referred to a "bubble point pressure." The bubble point pressure is an intrinsic characteristic of the particular filter-fluid combination. If the bubble point pressure is below a minimum value, then the filter has lost its integrity. If the bubble point pressure is above a minimum value, the filter passes the integrity test. The increase of the gas pressure and the detection of the liquid displacement (or bubble) are preferably coordinated and automated. As soon as a bubble is detected, the value of the gas pressure may be automatically recorded and the pressurization stopped. The recorded bubble point pressure may be directly reported, or it may be compared with a standard bubble point value for this type of sterile filter to determine whether the sterile filter 202 passes or fails the integrity test. The entire integrity test, starting from the supplying of the gas 22 and ending with the reporting of the bubble point pressure or the pass/fail decision, may be fully automated. For example, a user may initiate the integrity test by the push of a button, and a bubble point pressure or the pass/fail decision may be automatically displayed to the user as soon as the automated test is completed. Alternatively, the integrity test may be automatically initiated after a dispensing operation with no user interaction at all.

To ensure an accurate and prompt detection of a bubble regardless of variations in the tube 204 or the liquid 20, the detector 220 may be calibrated by taking at least two reference measurements prior to an integrity test. That is, a filled tube signal may be obtained when the tube 204 is filled with the liquid 20, and an empty tube signal may be obtained with the tube 204 is devoid of the liquid 20 (or filled with the gas 22 or empty). Based on the filled tube signal and the empty tube signal, the transition point from a full tube to an empty tube may be dynamically determined. The calibration may also be automated.

Figure 5:
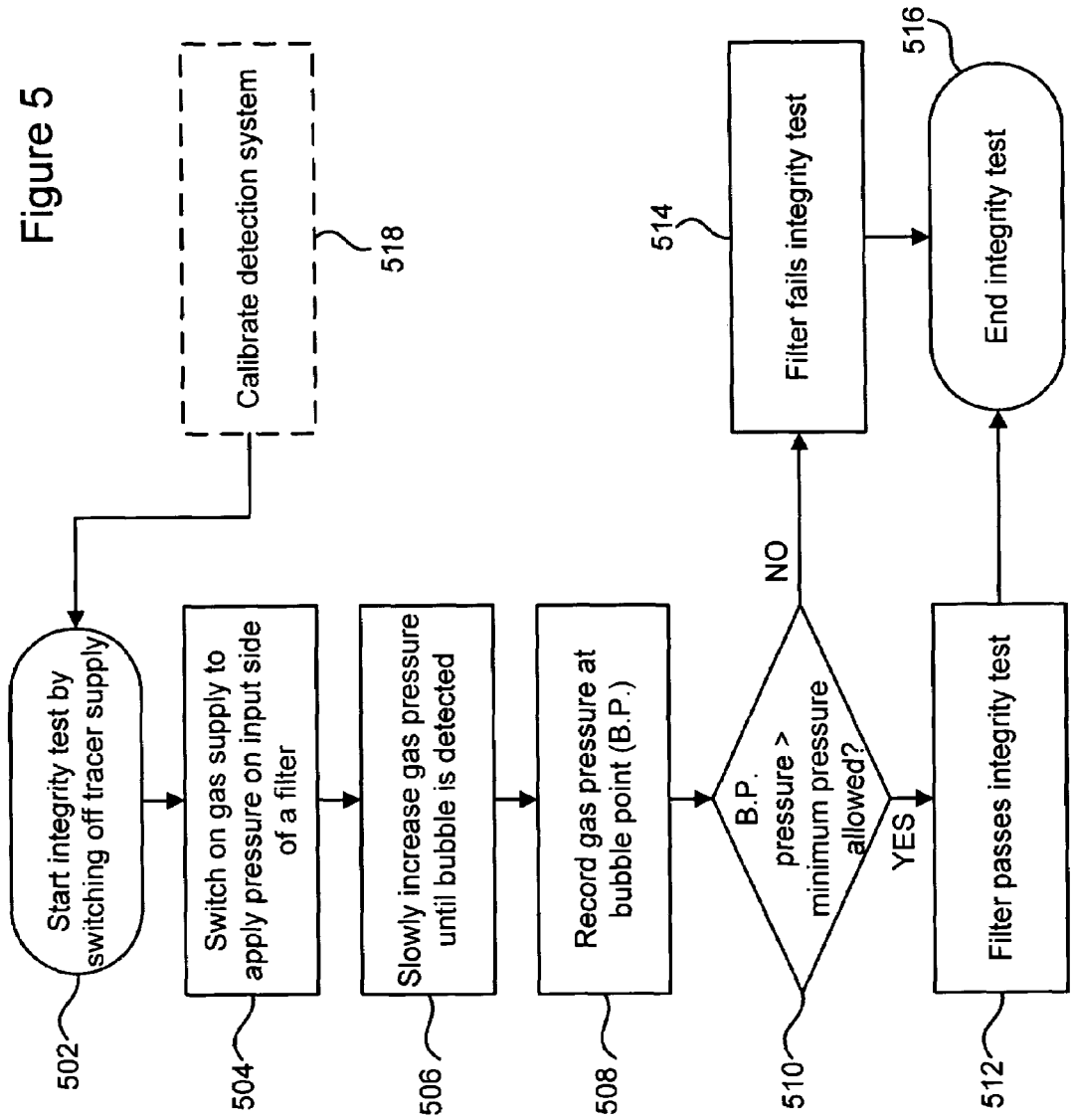
FIG. 5 is a flow chart illustrating an exemplary method for in-process integrity test of a filter according to an embodiment of the present invention.

FIG. 5 is a flow chart illustrating an exemplary method for in-process integrity test of a filter according to an embodiment of the present invention.

The in-process integrity test may be performed on a sterile filter while it is still installed in a radiotracer dispenser system. The integrity test may be started in step 502 by first switching off a supply of the radiotracer. Then, in step 504, a gas supply may be switched on to apply a controlled pressure on the input side of the sterile filter.

In step 506, the gas pressure may be slowly increased until one or more bubbles are detected on the output side of the sterile filter. The detection method may be the same as or similar to what is illustrated in FIGS. 2-4. To ensure an accurate and prompt detection of a bubble without being affected by variations in the tubing, the detection system may be optionally calibrated in step 518, typically sometime prior to the start of the integrity test.

In step 508, the value of the gas pressure at the bubble point may be recorded.

In step 510, it may be determined whether the recorded bubble point pressure is greater than a minimum pressure allowed. If so, the sterile filter passed the integrity test in step 512. The result of this test (i.e., pass or fail) may be a basis to determine whether a liquid that has just been dispensed through the sterile filter can be trusted as being sterile. Depending on how large the difference is between the recorded bubble point pressure and the minimum pressure allowed, the sterile filter may continue to be used to dispense and sterilize radiotracers. As the difference becomes smaller, that is, as the sterile filter approaches the end of its useful life, more frequent integrity tests may be performed on it until it eventually fails. This way, the sterile filter's usefully life may be more fully utilized.

If it is determined in step 510 that the recorded bubble point pressure is smaller than the minimum pressure allowed, the filter fails the integrity test in step 514. Then, the liquid that has just been dispensed through the sterile filter may be deemed defective and may be disqualified. In addition, the filter may be discarded.

The integrity test ends in step 516. However, since this in-process integrity test is fast and straightforward, the test may be repeated periodically, randomly, or as scheduled.

It should be noted that the above-described system and method for in-process integrity test of a filter may be easily adapted for in-process testing of any type of filter that might be subject to a bubble point test, and is not just limited to sterile filters used for radiotracers. In any system where a liquid is filled through a sterile filter and the filter needs an integrity test, the above-described technique may be implemented to eliminate the need of removing the filter from the system for off-line testing.

While the foregoing description includes many details, it is to be understood that these have been included for purposes of explanation only, and are not to be interpreted as limitations of the present invention. It will be apparent to those skilled in the art that other modifications to the embodiments described above can be made without departing from the spirit and scope of the invention. Accordingly, such modifications are considered within the scope of the invention as intended to be encompassed by the following claims and their legal equivalents.

What is claimed is:

1. A system for in-process integrity test of a filter, the system comprising:

a gas source coupled to an input side of a filter while the filter is still installed in a dispenser system, the gas source capable of supplying a gas and controlling a pressure of the gas;

a tube coupled to an output side of the filter, at least one portion of the tube being not opaque, wherein the at least one portion of the tube can be filled with a liquid;

a light source, on one side of the at least one portion of the tube, that is capable of passing a light beam at least once through the at least one portion of the tube;

a detector configured to detect the light beam after the light beam has passed at least once through the at least one portion of the tube, wherein the detection of the light beam indicates whether the liquid is displaced from the at least one portion of the tube by one or more gas bubbles; and a programmable logic control configured to determine a value of the pressure when a displacement of the liquid is detected.

2. The system according to claim 1, further comprising:

a container coupled to the tube configured to fill the tube with the liquid; and the programmable logic control further configured to gradually increase the pressure of the gas supplied to the input side of a filter.

3. The system according to claim 2, further comprising:

means for automatically recording the value of the pressure.

4. The system according to claim 1, further comprising:

a three-way switch that couples the gas source to the input side of the filter, wherein the other input of the three-way switch is coupled to a supply of the liquid.

5. The system according to claim 4, being configured to initiate the in-process integrity test of the filter with the three-way switch by stopping the supply of the liquid and supplying the gas to the input side of the filter.

6. The system according to claim 1, wherein the detector comprises a photoelectric sensor.

7. The system according to claim 1, further comprising:

a reflector, positioned on the other side of the at least one portion of the tube, that reflects the light beam to the detector, wherein the detector detects the light beam after the light beam passes twice through the at least one portion of the tube.

8. The system according to claim 1, wherein the detector is positioned on the other side of the at least one portion of the tube, and wherein the detector detects the light beam after the light beam passes once through the at least one portion of the tube.

9. The system according to claim 1, wherein the detector is configured to calibrate the detection of the light beam by:

detecting the light beam to obtain a filled tube signal when the at least one portion of the tube is filled with the liquid; and detecting the light beam to obtain an empty tube signal when the at least one portion of the tube is devoid of the liquid.

10. The system according to claim 1, wherein the light beam is provided through one or more optical fibers.

11. The system according to claim 1, wherein the at least one portion of the tube is transparent.

12. The system according to claim 1, wherein the at least one portion of the tube is partially transparent.

13. The system according to claim 1, wherein the dispenser system is an automated radiotracer dispenser system, and wherein the filter is a sterile filter.

* * * * *